United States Patent [19]

Nishiyama et al.

[11] Patent Number: 5,111,825

[45] Date of Patent: May 12, 1992

[54] ULTRASONIC DOPPLER FLOW METER

[75] Inventors: Hisashi Nishiyama, Tokyo; Toshio Ogawa, Chiba; Kageyoshi Katakura, Tokyo, all of Japan

[73] Assignee: Hitachi Medical Corporation, Tokyo, Japan

[21] Appl. No.: 609,657

[22] Filed: Nov. 6, 1990

[30] Foreign Application Priority Data

Nov. 8, 1989 [JP] Japan .................................. 1-288908

[51] Int. Cl.$^5$ .............................................. A61B 8/02
[52] U.S. Cl. .............................. 128/661.09; 73/861.25
[58] Field of Search ....................... 128/661.09, 661.07, 128/661.08, 661.10; 73/861.25

[56] References Cited

U.S. PATENT DOCUMENTS

| | | | |
|---|---|---|---|
| 4,809,703 | 3/1989 | Ishikawa et al. | 128/661.08 |
| 4,905,206 | 2/1990 | Nishiyama et al. | 128/661.09 |
| 4,955,386 | 9/1990 | Nishiyama et al. | 128/661.09 |
| 4,961,427 | 10/1990 | Namekawa et al. | 128/661.09 |
| 4,979,513 | 12/1990 | Sakai et al. | 128/661.09 |
| 4,993,417 | 2/1991 | Seo | 128/661.09 |

OTHER PUBLICATIONS

"Pulsed Ultrasonic Doppler Blood Flow Sensing," IEEE trans. SU-17, No. 3, pp. 170-185, 1970.
1978 Ultrasonic Symposium Proceedings, pp. 348-352.
"Real-Time Two Dimensional Blood Flow Imaging Using an Autocorrelation Technique." IEEE Trans. SU-32, No. 3 pp. 458-464, 1985.

*Primary Examiner*—Francis Jaworski
*Assistant Examiner*—George Manuel
*Attorney, Agent, or Firm*—Antonelli, Terry, Stout & Kraus

[57] ABSTRACT

A flow meter for detecting a flow speed in such a manner that an ultrasonic pulsed continuous wave is repeatedly transmitted toward an object at predetermined intervals T, a phase vector indicative of the phase of a reception signal due to the reflected wave is produced at the predetermined intervals, the phase difference between the present phase vector and the preceding phase vector is detected, and a Doppler frequency is calculated from the average value of a plurality of phase difference values to obtain the speed of the object. The phase difference values are classified into a first group consisting of position phase difference values and a second group consisting of negative phase difference values, the cosine and sine values of the central angle of the positive phase difference values and the cosine and sine values of the central angle of the negative phase difference values are calculated, and the argument of a vector indicated by the weighted sum of cosine values and the weighted sum of sine values is calculated to be used as an average phase angle.

10 Claims, 5 Drawing Sheets

ULTRASONIC DOPPLER FLOW METER

CROSS-REFERENCE TO RELATED APPLICATIONS

The present application relates to the subject matter described in application Ser. No. 611,541 filed on Nov. 13, 1990 (claiming priority based on Japanese Patent Application No. 01-292338 filed on Nov. 13, 1989), entitled "ULTRASONIC DOPPLER FLOW METER", by the same inventors and assigned to the same assignees of the present application.

BACKGROUND OF THE INVENTION

The present invention relates to a pulse doppler measuring apparatus, and more particularly to an apparatus for detecting the speed of a moving object by using an ultrasonic wave, for example, a pulse doppler measuring apparatus capable of measuring the flow speed of blood in a living body in realtime with a high signal-to-noise ratio.

Various kinds of apparatuses have hitherto been known which detect the flow speed of an object by utilizing the Doppler effect of an acoustic wave. Specifically, in an apparatus using the pulse Doppler method which is described in, for example, an article entitled "Pulsed Ultrasonic Doppler Blood Flow Sensing" by D. W. Baker (IEEE Trans. Vol. SU-17, No. 3, July 1970, pages 170 to 185), a pulsed continuous wave is sent out repeatedly, and a time gate corresponding to the distance to a measured part is set on a received signal to specify the measured part.

An ultrasonic Doppler blood flow measuring apparatus has been known, in which, as disclosed in, for example, JP-A-58-188433, JP-A-60-119929 and JP-A-61-25527, an ultrasonic wave is transmitted toward a blood vessel, and the Doppler shift frequency of the ultrasonic wave reflected from the blood in the blood vessel is measured to detect $v\cos\theta$, where $\theta$ represents an angle between the direction of blood flow and the transmission direction of the ultrasonic wave, and v indicates a blood flow speed.

Further, a technique called "color flow mapping", in which the distribution of blood flow speed in a cross section of a living body is measured and displayed in color on a tomographic image, is described in an article entitled "Real-Time Two-Dimensional Blood Flow Imaging Using an Autocorrelation Technique" by C. KASAI et al. (IEEE Trans. Vol. SU-32, No. 3, May 1985 pages 458 to 464). In order to carry out the color flow mapping at a desired image frame rate, the blood flow speed at each of a plurality of pixels is determined by averaging the measured values of Doppler shift due to a relatively small number of measurements. In the example mentioned in the above article, a difference vector between a vector indicated by a Doppler signal detected currently and a vector indicated by the preceding Doppler signal is obtained by an autocorrelator for each of the measurements, and the average speed is calculated from the argument of a vector which represents the sum of a plurality of difference vectors. That is, the autocorrelation method is used in the above example.

Meanwhile, U.S. Pat. No. 4,809,703 discloses the so-called two axial component method, in which a phase difference $\Delta\theta$ of a Doppler signal obtained for each measurement is decomposed into a cosine component and a sine component, a plurality of values of each of the cosine and sine components are added and averaged, and a phase difference indicated by the average cosine and sine components thus obtained is transformed into a velocity.

Further, an article entitled "Blood Flow Imaging Using a Discrete-Time Frequency Meter" by M. A. Brandestini and F. K. Forster (1978 Ultrasonics Symposium Proceedings pages 348 to 352) shows a method in which the phase difference of a Doppler signal is detected for each of a plurality of repetitions of measurement, and an average phase difference is calculated by adding a plurality of values of phase difference directly, to be converted into a velocity. This method will hereinafter be referred to as "phase difference averaging method".

Meanwhile, it is pointed out in U.S. Pat. No. 4,905,206 that the phase difference averaging method produces a large calculation error when a true average phase difference is close to $+\pi$ or $-\pi$, that is, a moving object is put in a high-speed region, and that the autocorrelation method and the two axial component method produce a large calculation error when the true average phase difference is close to zero, that is, the moving object is put in a low-speed region. U.S. Pat. No. 4,905,206 further discloses that one of the phase difference averaging method and the autocorrelation method (or the two axial component method) can be changed over to the other so that the above difficulties are eliminated, and that values of phase difference obtained for a plurality of measurements are transformed into those in a new polar coordinate system using a direction which is indicated by the average phase difference angle according to the autocorrelation method, as a reference axis, and the values of phase difference thus obtained are added and averaged.

SUMMARY OF THE INVENTION

The further investigation conducted by the present inventors has shown that the calculation of an average phase difference in the new polar coordinate system which is described in U.S. Pat. No. 4,905,206 fails to eliminate the sources of the errors completely. In other words, the new polar coordinate system is formed so that the direction of a central angle indicative of an average value of dispersed phase difference values obtained for a plurality of measurements is used as a reference axis to bring phase difference values which are to be averaged close to $\pm 0$. However, when the average phase difference for determining the reference axis is calculated by the autocorrelation method, a large error is produced in the low speed region, because the measured phase difference value fluctuates widely on the basis of noise. In such a case, the reference axis of the new polar coordinate system does not agree with the direction of the central angle of the dispersed phase difference values. That is, an angle greater than $\pi$ and an angle less than $-\pi$ are folded back, and thus it is impossible to perform a correct arithmetic operation for obtaining an average phase difference.

It is accordingly an object of the present invention to provide an ultrasonic Doppler flow meter capable of producing an output which does not deviate from a true average flow speed much, even when the phase difference detected for each measurement varies widely.

It is another object of the present invention to provide an ultrasonic Doppler flow meter which can carry out the phase difference averaging method appropriately even when the detected phase difference value varies widely, and thus can reduce an error in measurement greatly.

According to an aspect of the present invention, there is provided an ultrasonic Doppler flow meter which comprises means for classifying a plurality of phase difference values detected from a reflected ultrasonic wave into a first group consisting of positive phase difference values and a second group consisting of negative phase difference values, means for calculating an average value of the phase difference values belonging to the first group to obtain cosine and sine values of an angle indicated by the average value, means for calculating an average value of the phase difference values belonging to the second group to obtain cosine and sine values of an angle indicated by the average value, means for adding the cosine components while using a weight corresponding to one of the number of phase difference values included in each of the first and second groups and the power of each phase difference signal, and for adding the sine components while using a weight corresponding to one of the number of phase difference values included in each of the first and second groups and the power of each phase difference signal, and means for calculating the argument of a vector of which the real and imaginary parts are given by the sum of the cosine components and the sum of the sine components, respectively, to obtain a total average phase difference.

According to another aspect of the present invention, there is provided an ultrasonic Doppler flow meter which comprises the above means, and in which a plurality of measured phase difference values are transformed into values in a new polar coordinate system using a direction which is indicated by the total average phase difference angle, as a reference axis, and the phase difference values in the new polar coordinate system are added and averaged, to transform the average value thus obtained into a velocity.

According to the calculation of the total average phase difference based upon the grouping of measured phase difference values, even when the phase difference value obtained for each measurement varies widely, a large error due to the autocorrelation method and the conventional two axial component method will never appear. Accordingly, when the total average phase difference is transformed into a velocity, a flow speed is obtained which is hardly affected by noise.

Further, the total average phase difference does not deviate so greatly from the center value of dispersed phase difference values obtained for a plurality of measurements. Accordingly, the direction indicated by the total average phase difference angle is suited to be used as the reference axis of a new polar coordinate system which is introduced to add and average angles (namely, phase difference angles).

Other features and advantages of the present invention will become apparent from the following detailed explanation taken in conjunction with the accompanying drawings.

DESCRIPTION OF THE PREFERRED EMBODIMENTS

The principle of the present invention and embodiments thereof will be explained below in detail, with reference to the drawings. First, explanation will be made of the outline of the construction of a pulse Doppler measuring apparatus according to the present invention and the operation principle of the apparatus.

Figure 1:
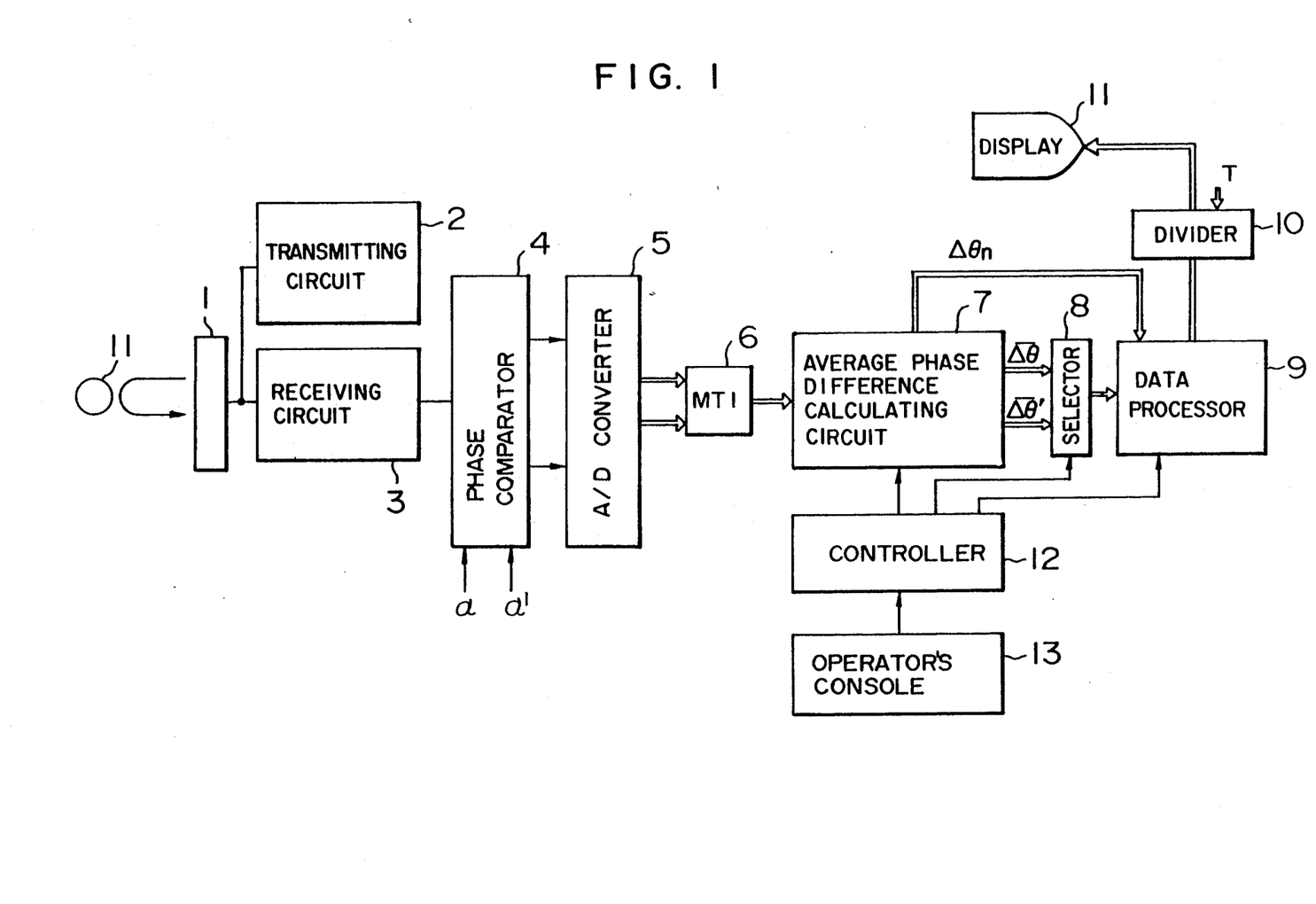
FIG. 1 is a block diagram showing the whole construction of an embodiment of a pulse Doppler measuring apparatus according to the present invention.

FIG. 1 is a block diagram showing an embodiment of a pulse Doppler measuring apparatus according to the present invention.

The present embodiment includes a transmitting circuit 2, a receiving circuit 3, a phase comparator 4, an A/D converter 5, a fixed substance removing filter, that is, an MTI (moving target indication) filter 6, an average phase difference calculating circuit 7, a selector 8 for changing an output, a data processor 9, a divider 10, a display device 11, a controller 12, and an operator's console 13. The transmitting circuit 2 gives a pulsed continuous wave to a transducer 1 at intervals of a predetermined time T. Thus, the transducer 1 emits an ultrasonic pulsed continuous wave toward a reflecting body 11 at intervals of T. The reflected acoustic wave thus produced is incident on the transducer 1, and the reflection signals therefrom are successively detected by the receiving circuit 3. In the phase comparator 4, each of the detected received signals is mixed with two kinds of reference signals $\alpha = A\cos\omega t$ and $\alpha' = A\sin\omega_0 t$, to obtain Doppler signals $V_R$ and $V_I$ having phase information of the reflection signal. In the A/D converter 5, the signals $V_R$ and $V_I$ of the wave reflected from the reflecting body 11 located at a predetermined depth are sampled at intervals of T, to be transformed into digital signals. The digital signals thus obtained are expressed b $V'_{Rn}$ and $V'_{In}$, when the number of the repetition of ultrasonic transmission is indicated by n (= 1, 2, 3, and so on). The signals $V'_{Rn}$ and $V'_{In}$ are given by the following equations:

$$V'_{Rn} = A_n \cos\theta'_n \quad (1)$$

$$V'_{In} = A_n \sin\theta'_n \quad (2)$$

The MTI filter 6 produces a first-order difference of the output of the A/D converter 5, to remove the unvaried reflected wave signal coming from a fixed substance. For the sake of simplicity, let us rewrite the equations (1) and (2) as follows:

$$V'_n = A_n exp(j\theta'_n) \quad (3)$$

Then, the output $V_n$ of the MTI filter is given by the following equation:

$$V_n = V'_n - V'_{n-1} \quad (4)$$

The output $V_n$ will hereinafter be referred to as "phase vector".

Figure 2:
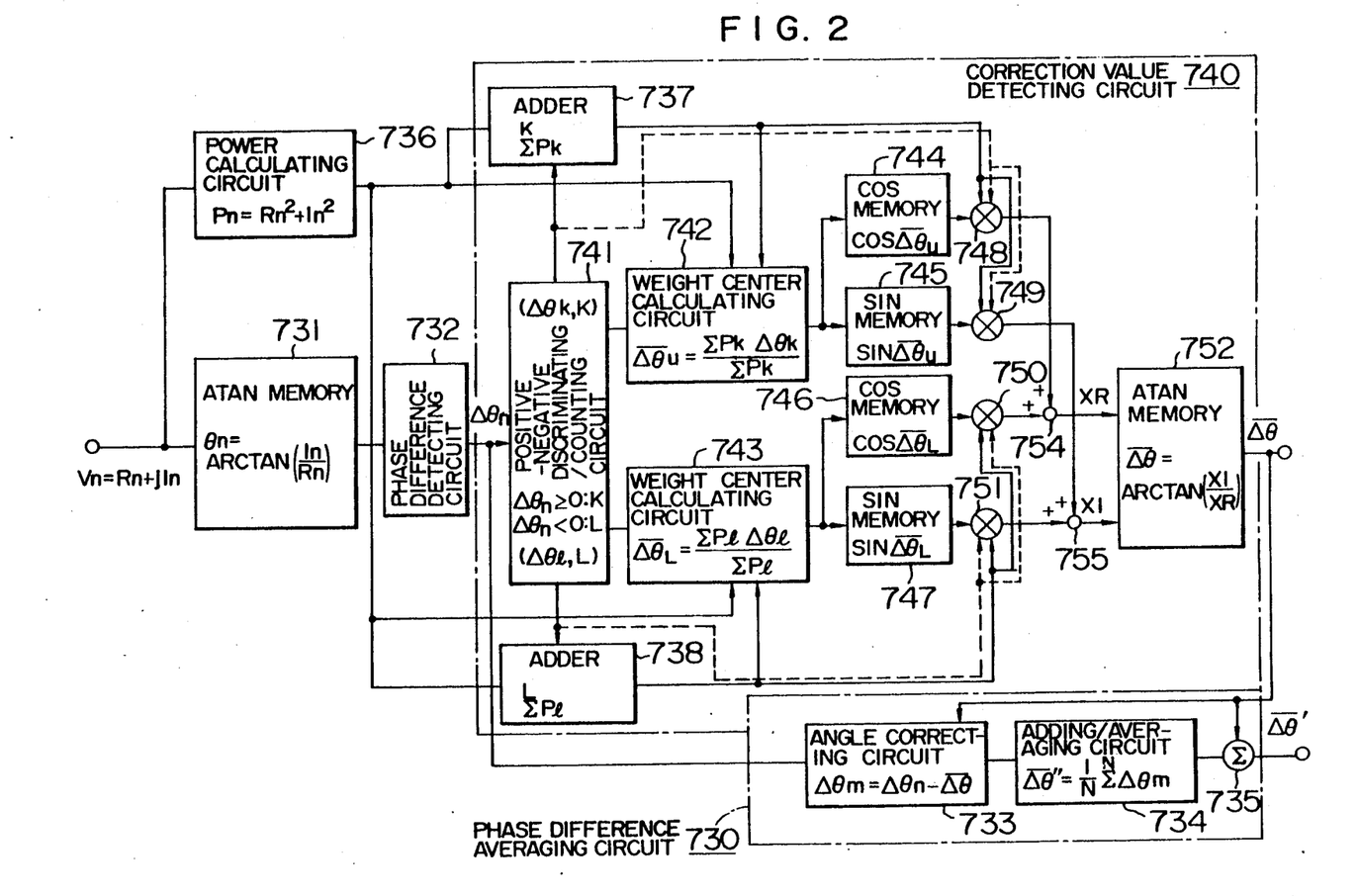
FIG. 2 is a block diagram showing a main part of the embodiment of FIG. 1 in detail.

FIG. 2 shows an example of the average phase difference calculating circuit 7. Referring to FIG. 2, each time the phase vector $V_n$ is supplied from the MTI filter to a power calculating circuit, the power calculating circuit calculates the power $P_n$ of the phase vector from the real part $R_n$ and imaginary part $I_n$ of the phase vector in accordance with the following equation:

$$P_n = R_n^2 + I_n^2 \tag{5}$$

The phase vector $V_n$ is also applied to an ATAN memory 731. The memory 731 stores therein a transformation table for obtaining the argument of the phase vector from the values of real and imaginary parts thereof, to deliver the phase angle (that is, argument) $\theta_n$ of the phase vector $V_n$. A phase difference detecting circuit 732 produces the difference between a phase vector at the present time and a phase vector at the time preceding by one time period, to obtain a phase difference $\Delta\theta_n$. It is to be noted that the phase difference $\Delta\theta_n$ is detected as an angle lying in a range from $+\pi$ to $-\pi$, and thus is given by the following equation:

$$\begin{aligned}\Delta\theta_n &= \theta_n - \theta_{n-1} &&\text{for } |\theta_n - \theta_{n-1}| \leq 180° \\ &= \theta_n - \theta_{n-1} - 360° &&\text{for } \theta_n - \theta_{n-1} > 180° \\ &= \theta_n - \theta_{n-1} + 360° &&\text{for } \theta_n - \theta_{n-1} < 180°\end{aligned} \tag{6}$$

Phase difference values $\Delta\theta_n$ thus obtained are successively applied to each of a correction value detecting circuit 740 and a phase difference averaging circuit 730.

The correction value detecting circuit 740 and the phase difference averaging circuit 730 calculate values $\overline{\Delta\theta}$ and $\overline{\Delta\theta'}$ of average phase difference, respectively, by a method peculiar to the present invention, each time a predetermined number N of phase difference data $\Delta\theta_n$ (for example, eight or sixteen phase difference data) are applied to the circuits 740 and 730. The above method will be explained below.

In the correction value detecting circuit 740, a positive-negative discriminating/counting circuit 741 discriminates between positive phase difference data and negative phase difference data, counts the number K of positive phase difference data and the number L of negative phase difference data, and delivers positive phase difference data $\Delta\theta_k$ (where k=1, k) and negative phase difference data $\Delta\theta_l$ (where l=1, L) separately. That is, the above operation is written as follows:

$$\begin{aligned}\Delta\theta_n \geq 0 &\rightarrow K \rightarrow \Delta\theta_k \text{ (where } k = 1, K) \\ \Delta\theta_n < 0 &\rightarrow L \rightarrow \Delta\theta_l \text{ (where } l = 1, L)\end{aligned} \tag{7}$$

The positive phase difference data $\Delta\theta_k$ (where k=1, ... K) are successively applied to a weight center calculating circuit 742, in which an average value $\overline{\Delta\theta_u}$ of the positive phase difference data $\Delta\theta_k$ is calculated. In more detail, those ones $P_k$ of power values $P_n$ delivered from the power calculating circuit 736 which correspond to the positive phase difference data $\Delta\theta_k$ are added by an adder 737 to obtain $$\sum_{k}^{K} P_k.$$

The sum $$\sum_{k}^{K} P_k$$

obtained from the adder 733 which sequentially add the $P_k$ is used to perform a weighted, averaging operation as follows:

$$\overline{\Delta\theta_u} = \frac{\sum_{k}^{K} P_k \cdot \Delta\theta_k}{\sum_{k}^{K} P_k} \tag{8}$$

Meanwhile, those ones $P_l$ of power values $P_n$ which correspond to the negative phase difference data $\Delta\theta_l$ are added by an adder 738 to obtain $$\sum_{l}^{L} P_l.$$

The negative phase difference $\Delta\theta_l (l=1, \ldots$ is applied to another weight center calculating circuit 743, to perform a weighted, averaging operation as follows:

$$\overline{\Delta\theta_L} = \frac{\sum_{l}^{L} P_l \cdot \Delta\theta_l}{\sum_{l}^{L} P_l} \tag{9}$$

The average value $\overline{\Delta\theta_u}$ thus obtained indicates the weight center of the phase difference angles $\Delta\theta_n$ in the first and second quadrants, and the average value $\overline{\Delta\theta_L}$ indicates the weight center of the phase difference angles $\Delta\theta_n$ in the third and fourth quadrants.

A COS memory 744 stores therein a transformation table for transforming an angle into the cosine value thereof, and a SIN memory 745 stores therein a transformation table for transforming an angle into the sine value thereof. The central angle $\overline{\Delta\theta_U}$ is applied to the memories 744 and 745 to obtain the cosine and sine values of the angle $\overline{\Delta\theta_U}$. Similarly, the central angle $\overline{\Delta\theta_L}$ is applied to a COS memory 746 and a SIN memory 747 to obtain the cosine and sine values of the angle $\overline{\Delta\theta_L}$. The cosine components thus obtained are added by an adder 754 in the following special manner. The cosine value $\cos \overline{\Delta\theta_U}$ outputted from the COS memory 744 is multiplied by the power sum $$\sum_{k}^{K} P_k$$

corresponding to the positive phase difference by means of a multiplier 748 and the cosine value $\cos\overline{\Delta\theta_L}$ outputted from the COS memory 746 is multiplied by the power sum $$\sum_{l}^{L} P_l$$

corresponding to the negative phase difference by means of a multiplier 750. The outputs of the multipliers 748 and 750 are added by an adder 754. That is, weighted addition is carried out for the cosine values $\cos\overline{\Delta\theta_U}$ and $\cos\overline{\Delta\theta_L}$. Similarly, the sine value $\sin\overline{\Delta\theta_U}$ outputted from the SIN memory 745 is multiplied by the power sum $$\sum_{k=1}^{K} P_k$$

by means of a multiplier 749, and the sine value $\sin\Delta\theta_l$ outputted from the SIN memory 747 is multiplied by the power sum $$\sum_{l=1}^{L} P_l$$

by means of a multiplier 751. The outputs of the multipliers 749 and 751 are added by an adder 755. That is, weighted addition is carried out for the sine values $\sin\overline{\Delta\theta}_U$ and $\sin\overline{\Delta\theta}_L$. Respective outputs XR and XI of the adders 754 and 755 are given by the following equations:

$$X_R = \sum_{k=1}^{K} P_k \cos\overline{\Delta\theta}_U + \sum_{l=1}^{L} P_l \cos\overline{\Delta\theta}_L$$
$$X_I = \sum_{k=1}^{K} P_k \sin\overline{\Delta\theta}_U + \sum_{l=1}^{L} P_l \sin\overline{\Delta\theta}_L$$
(10)

As mentioned above, the weight center of positive phase difference angles and the weight center of negative phase difference angles are delivered from the weight center calculating circuits 742 and 743, respectively. Alternatively, the simple average angle of the positive phase difference angles and the simple average angle of the negative phase difference angles may be calculated by the circuits 742 and 743, respectively. That is, the output $\overline{\Delta\theta}_U$ and $\overline{\Delta\theta}_L$ of the circuits 742 and 743 are calculated not by the equations (8) and (9) but by the following equations:

$$\overline{\Delta\theta}_U = \frac{\sum_{k=1}^{K} \Delta\theta_k}{K}$$
(11)

$$\overline{\Delta\theta}_L = \frac{\sum_{l=1}^{L} \Delta\theta_l}{L}$$
(12)

In this case, the power calculating circuit 736 and the adders 737 and 738 can be omitted, and signal lines which extend from the positive-negative discriminating/counting circuit 741 and is indicated by a broken line in FIG. 2 is used. Further, in the multipliers 748 and 750, the number K of positive phase difference data $\Delta\theta_k$ is used as a weight coefficient in place of the power sum $$\sum_{k=1}^{K} P_k.$$

In the multipliers 749 and 751, the number L of negative phase difference data $\Delta\theta_l$ is used as a weight coefficient in place of the power sum $$\sum_{l=1}^{L} P_l.$$

In the above case, the output $X_R$ of the adder 754 and the output $X_I$ of the adder 755 are given by the following equations:

$$X_R = K\cos\overline{\Delta\theta}_U + L\cos\overline{\Delta\theta}_L$$
$$X_I = K\sin\overline{\Delta\theta}_U + L\sin\overline{\Delta\theta}_L$$
(13)

An ATAN memory 752 stores therein a transformation table for obtaining the argument of a vector from the values of real and imaginary parts of the vector. The outputs $X_R$ and $X_I$ of the adders 754 and 755 are applied to the ATAN memory 752, which delivers the argument $\overline{\Delta\theta}$ of a vector X given by the following equation:

$$X = X_R + jX_I$$
(14)

The argument $\overline{\Delta\theta}$ is given by the following equation:

$$\overline{\Delta\theta} = \tan^{-1}(X_I/X_R)$$
(15)

The value of argument $\overline{\Delta\theta}$ thus obtained is delivered as the output of the correction value detecting circuit 740. The argument $\overline{\Delta\theta}$ is an average phase difference which is obtained in such a manner that N phase difference data are classified into a first group consisting of positive phase difference data and a second group consisting of negative phase difference data, a central or average angle of phase difference angles belonging to the first group and a central or average angle of phase difference angles belonging to the second group are calculated, each central (or average) angle is transformed into cosine and sine values thereof, and an average value of cosine values and an average value of sine values are calculated. When the above average values are calculated, the power sum corresponding to each of the first and second groups or the number of phase difference data included in each of the first and second groups is used as a weight coefficient. Hence, the argument $\overline{\Delta\theta}$ indicates a substantially central value of N dispersed phase difference data.

In the present embodiment, it is possible to select one of two modes, that is, a mode in which the value of $\overline{\Delta\theta}$ is transformed into a velocity and the velocity thus obtained is displayed as an average flow speed, and a mode in which the value of $\overline{\Delta\theta}$ is used as a correction value, that is, N phase difference data are transformed into values in a new polar coordinate system using the direction indicated by $\overline{\Delta\theta}$ as a reference axis, and the values in the new polar coordinate system are added and averaged to obtain a more accurate average phase difference. In the phase difference averaging circuit of FIG. 2, N phase difference data in the new polar coordinate system are added and averaged. That is, in an angle correcting circuit 733, the correction value $\overline{\Delta\theta}$ is subtracted from each phase difference data $\Delta\theta_n$, and the principal value of the difference angle $\Delta\theta_n - \overline{\Delta\theta}$ is determined. When this principal value is expressed by $\Delta\theta_m$, the principal value $\Delta\theta_m$ is given by the following equation:

$$\begin{aligned}\Delta\theta_m &= \Delta\theta_n - \overline{\Delta\theta} & \text{for } |\Delta\theta_n - \overline{\Delta\theta}| \leq 180° \\ &= \Delta\theta_n - \overline{\Delta\theta} - 360° & \text{for } \Delta\theta_n - \overline{\Delta\theta} > 180° \\ &= \Delta 74_n - \overline{\Delta\theta} + 360° & \text{for } \Delta\theta_n - \overline{\Delta\theta} < 180°\end{aligned}$$
(16)

In an adding/averaging circuit 734, N phase difference data $\Delta\theta_m$ thus obtained are added and averaged.

Thus, the output $\overline{\Delta\theta''}$ of the circuit 734 is given by the following equation:

$$\overline{\Delta\theta''} = \frac{1}{N}\sum_{m=1}^{N}\Delta\theta_m \quad (17)$$

The value of $\overline{\Delta\theta''}$ is the average value of phase difference data $\Delta\theta_m$ in the new polar coordinate system where the direction indicated by the output $\overline{\Delta\theta}$ of the correction value detecting circuit 740 is used as the reference axis, an angle in a range from 0° to 180° is defined in the counterclockwise direction from the reference axis, and an angle in a range from 0° to −180° is defined in the clockwise direction from the reference axis. Accordingly, an error which is produced in averaging phase difference data distributed in the vicinity of $\pm\pi$, is reduced, and an accurate average value is obtained. In an adder 735, the correction value $\overline{\Delta\theta}$ is added to the average value $\overline{\Delta\theta''}$ to carry out inverse transformation for the average value $\overline{\Delta\theta''}$. Thus, the average value $\overline{\Delta\theta''}$ is transformed into an average phase difference $\overline{\Delta\theta'}$ in an original polar coordinate system. The average phase difference $\overline{\Delta\theta'}$ is given by the following equation:

$$\overline{\Delta\theta'} = \overline{\Delta\theta''} + \overline{\Delta\theta} \quad (18)$$

As mentioned above, in the average phase difference calculating circuit 7, two kinds of average phase difference data $\overline{\Delta\theta}$ and $\overline{\Delta\theta'}$ are calculated each time N phase vectors are detected.

Referring back to FIG. 1, one of $\overline{\Delta\theta}$ and $\overline{\Delta\theta'}$ is selected by the selector 8 in accordance with a control signal which is sent out from the controller 12 on the basis of a command from the operator's console 13 to be applied to the data processor 9. After having been subjected to necessary processing in the data processor 9, the selected average phase difference $\overline{\Delta\theta}$ or $\overline{\Delta\theta'}$ is applied to the divider 10 to be divided by the transmission interval T of the ultrasonic wave, thereby being transformed into a Doppler angular frequency $\omega_d$. That is, the Doppler angular frequency $\omega_d$ is given as follows:

$$\left. \begin{array}{l} \omega_d = \overline{\Delta\theta}/T \\ \text{or} \\ \omega_d = \overline{\Delta\theta'}/T \end{array} \right\} \quad (19)$$

In the present embodiment, the data processor 9 stores therein a phase difference correcting program. Accordingly, even if the average phase difference $\overline{\Delta\theta'}$ obtained in the above manner has a calculation error, the average phase difference $\overline{\Delta\theta'}$ can be corrected.

The phase difference correcting program uses a basic algorithm which is applicable to various methods of adding and averaging phase difference data. In more detail, when one true phase difference data exceeds 180° in a process for adding phase difference data, the true phase difference data is folded back, and thus the result of addition will differ from the true sum by −360°. Accordingly, the average value of N phase difference data will differ from a true average value by −360°/N. When two true phase difference data exceed 180°, the average value of N phase difference data will differ from a true average value by −720°/N. Further, when one true phase difference data is less than −180°, the value of phase difference data will differ from a true average value by 360°/N. The function of the phase difference correcting program is to presume a plurality of average values having such errors and to estimate the presumed average values for the purpose of selecting the most appropriate average value.

Figure 3:
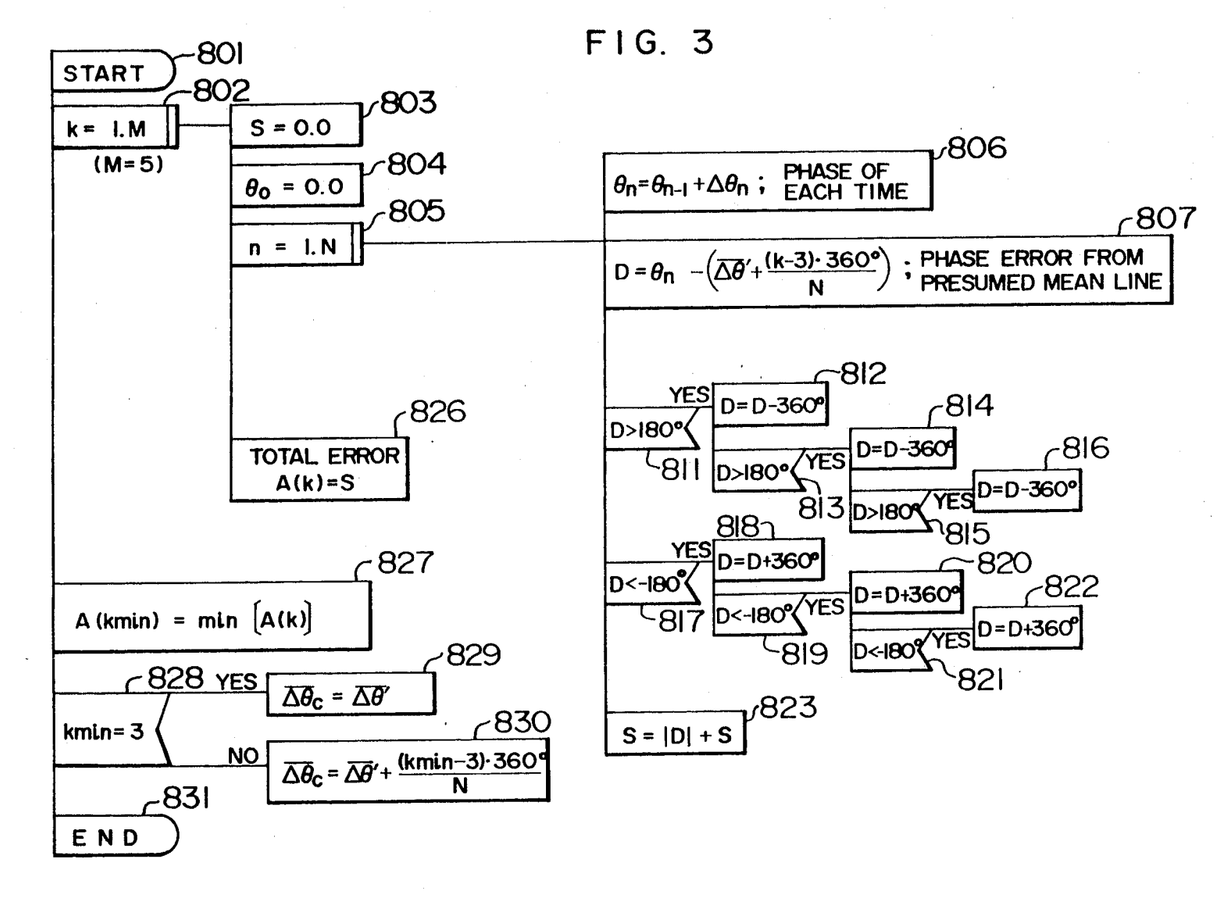
FIG. 3 is a problem analysis diagram showing a program which is executed by the data processor of FIG. 1.
Figure 4:
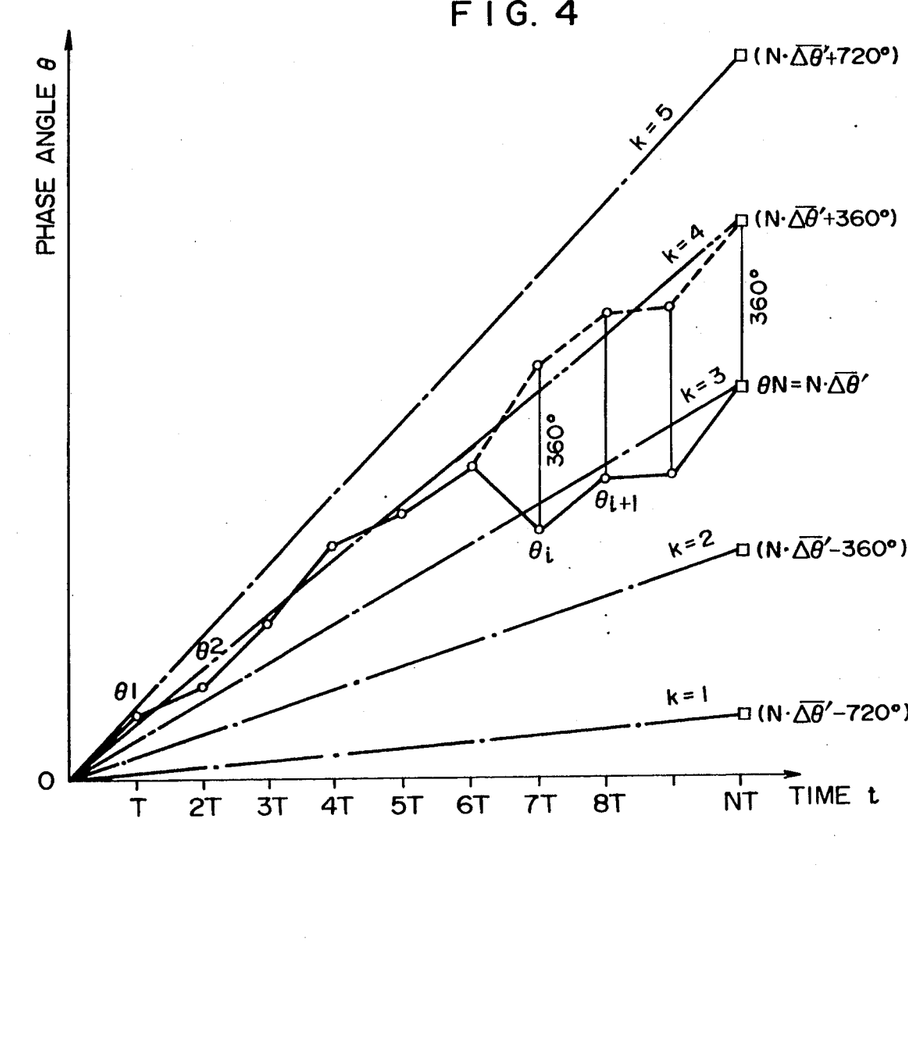
FIG. 4 is a graph which shows a phase change characteristic for explaining the function of the program of FIG. 3.

FIG. 3 shows an example of the phase difference correcting program in the form of a problem analysis diagram (PAD). In the present example, five kinds of presumed average values are estimated. Referring to FIG. 3, the program is started (step 801). In step 802, the number k of the repetition of processing is specified in a range from 1 to M (M=5 in the present example). Repeated processing includes steps 803 to 805. In the step 803, the initial value of an error S is set to zero. In the step 804, the initial value $\theta_0$ of an angle is set to zero. In the step 805, the number of the repetition of processing is specified in a range from 1 to N (where N indicates the number of angles to be averaged). The contents of the repeated processing are as follows. In step 806, phase difference data $\Delta\theta_1$ to $\Delta\theta_N$ from the phase difference detecting circuit 732 are successively summed up to obtain $\theta_n$. FIG. 4 shows the change of $\theta_n$ with the number n (where n=1, 2, ... N). Meanwhile, by using the average value $\overline{\Delta\theta'}$ from the average phase difference calculating circuit 7, five presumed average values to be estimated are given by the following equation:

$$\overline{\Delta\theta}_k = \overline{\Delta\theta'} + \frac{(k-3) \times 360°}{N} \quad (20)$$

(where $n = 1, 2, 3, 4$ and 5)

Now, let us assume a case where phase difference data are not dispersed at all, and each phase difference data is equal to the average phase difference $\overline{\Delta\theta}_k$. In this case, the value $\theta_n$ which is obtained by summing up the phase difference data successively will travel on one of five dot-dash lines shown in FIG. 4. In step 807, the difference D between the sum $\theta_n$ of actual phase difference data $\Delta\theta_1$ to $\Delta\theta_n$ and a corresponding value on the dot-dash line is calculated as follows:

$$D = \theta_n - \left(\overline{\Delta\theta'} + \frac{(k-3) \times 360°}{N}\right) \times n \quad (21)$$

In steps 811 to 822, the difference angle D is transformed into a principal value (namely, an angle within a range from −180° to +180°). In step 823, the absolute value of the principal value of the difference angle D is added to the error S which is obtained at the preceding stage, to update the error S. This processing is repeated till the number n becomes N. The value of S thus obtained is an index for indicating the degree of coincidence between the solid line shown in FIG. 4 and one of the dot-dash lines. Accordingly, in step 826, the above error S is used as a total error A(k). In the step 802, the above processing is repeated for values 1 to M of the number k. Thus, five total errors A(1) to A(5) for indicating the degree of coincidence between the solid line of FIG. 4 and each of five dot-dash lines are obtained. Strictly speaking, the total error A(k) does not indicate the total sum of errors between the solid line and one of the dot-dash lines, but indicates the total sum of absolute values of principal values of the above errors, since the program includes the process of the steps 811 to 822 for transforming the difference angle D into a principal value. When the repetition in the step 802 is completed, five values of total error A(k) for k=1, 2, 3, 4, 5 are compared with one another to find the smallest one of five values, and the number k producing the smallest total error is referred to as "$k_{min}$" (step 827). Thus, that one of five dot-dash lines which can indicate a correct average value more appropriately than the remaining dot-dash lines is determined. In steps 828 and 829, the most appropriate average value $\overline{\Delta\theta_c}$ is given by the following equation:

$$\overline{\Delta\theta_c} = \overline{\Delta\theta'} + \frac{(k_{min} - 3) \times 360°}{N} \tag{22}$$

Specifically, the average value $\overline{\Delta\theta_c}$ for $k_{min}=3$, as shown in step 829, is given by the following equation:

$$\overline{\Delta\theta_c} = \overline{\Delta\theta'} \tag{23}$$

The solid line of FIG. 4 shows a case where the true value of the i-th phase difference exceeds 180°, and is folded back. In this case, the average value $\overline{\Delta\theta'} + 360°/N$ for k=4 is a correct average value. According to the above-mentioned program, the i-th and following phase difference data are transformed into principal values on the broken line of FIG. 4 by the processing in the steps 811 to 822, and the difference between each of the values thus obtained and a corresponding value on the dot-dash line for k=4 is used to update the error S. Accordingly, it is judged by calculation that the total error A(4) is the smallest one of the errors A(1), A(2), A(3), A(4) and A(5). Thus, the correct average value is selected.

The average phase difference which has been checked by the phase difference correcting program is transformed by the divider 10 into a speed value which is displayed on the display screen of the display device 11. It is indicated by the operator's console 13 whether or not the phase difference correcting program is used for the average value $\overline{\Delta\theta'}$ outputted from the average phase difference calculating circuit 7. Further, speed values corresponding to the average values $\overline{\Delta\theta}$, $\overline{\Delta\theta'}$ and $\overline{\Delta\theta_c}$ can be displayed on the display screen in parallel.

Figure 5:
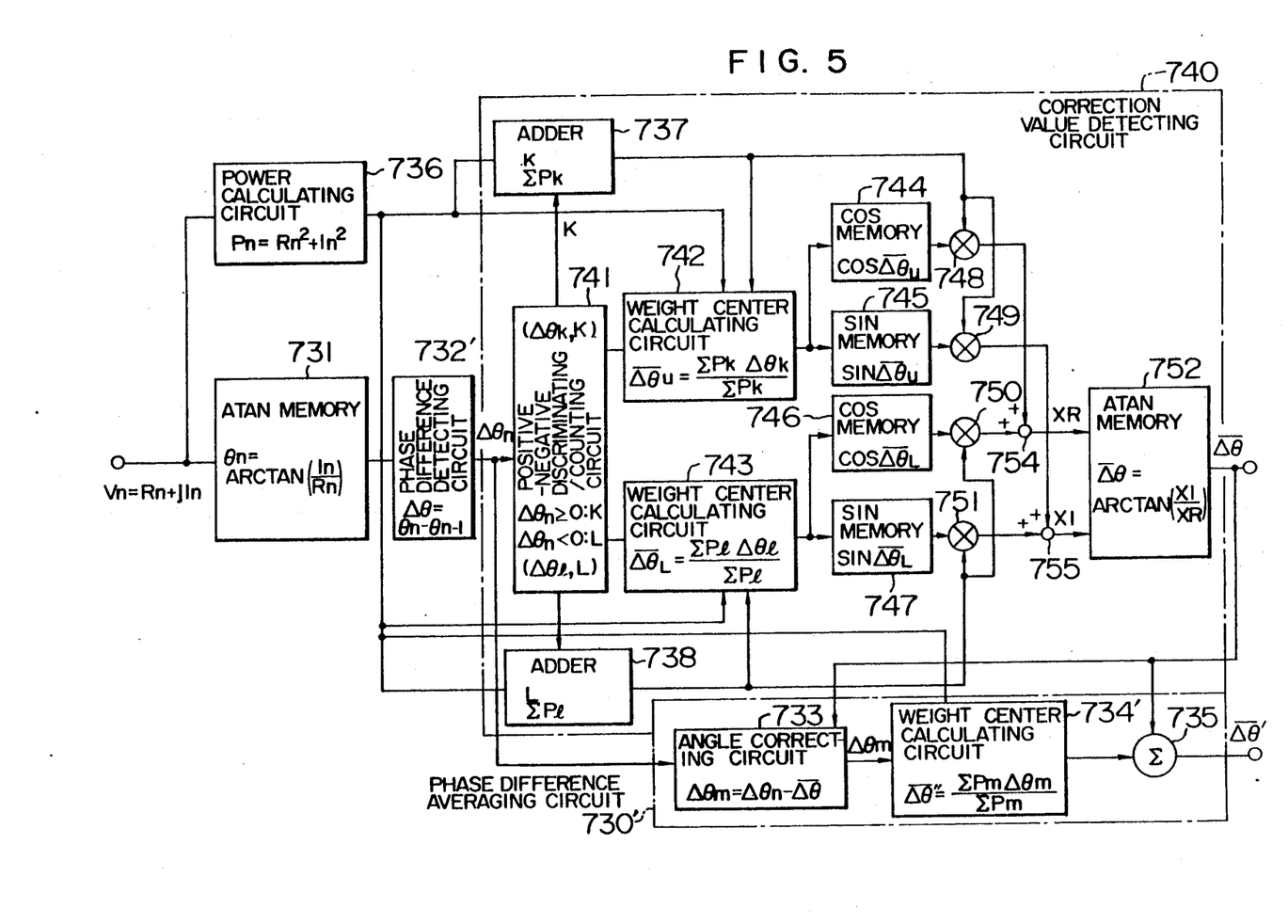
FIG. 5 is a block diagram showing a main part of another embodiment of a pulse Doppler measuring apparatus according to the present invention, in detail.

FIG. 5 shows another example of the average phase difference calculating circuit 7. In FIG. 5, the ATAN memory 731, the phase difference detecting circuit, 732, the power calculating circuit 736 and the correction value detecting circuit 740 are equal in construction to those shown in FIG. 2. Accordingly, each of these circuits performs the same operation as mentioned above. In the correction value detecting circuit 740, the central angle of positive ones of phase difference data $\Delta\theta_n$ and the central angle of negative phase difference data are calculated, each central angle is transformed into cosine and sine values thereof, and the correction value $\overline{\Delta\theta}$ indicative of the substantially central angle of dispersed phase difference data $\Delta\theta_n$ is calculated from the sum of cosine values and the sum of sine values. Meanwhile, in a phase difference averaging circuit 730', the phase difference data $\Delta\theta_n$ are transformed into values $\Delta\theta_m$ in a new polar coordinate system where the direction indicated by the correction value $\overline{\Delta\theta}$ is used as a reference axis, and not the simple arithmetic mean of phase difference data $\Delta\theta_m$ but the central angle thereof is calculated by utilizing the output $P_n$ of the power calculating circuit 736. That is, in the angle correcting circuit 733, each phase difference data $\Delta\theta_n$ is transformed on the basis of the equation (16) into the angle $\Delta\theta_m$ in the new polar coordinate system where the direction of the correction angle $\overline{\Delta\theta}$ is used as the reference axis. In a weight center calculating circuit 734', the power $P_m$ of each phase signal delivered from the power calculating circuit 736 is used as a weight coefficient (it is to be noted that the power $P_n$ of the phase signal indicating the phase difference $\Delta\theta_n$ is the same as the power $P_m$ of the phase signal indicating the phase difference $\Delta\theta_m$ and thus the output of the power calculating circuit 736 may be expressed by $P_m$), and central angle of phase difference data $\Delta\theta_m$ (that is, central phase difference angle $\overline{\Delta\theta''}$) is calculated by the following equation:

$$\overline{\Delta\theta''} = \frac{\sum\limits_{m=1}^{M} P_m \Delta\theta_m}{\sum\limits_{m=1}^{M} P_m} \tag{24}$$

In the adder 735, as in FIG. 2, the correction angle $\overline{\Delta\theta}$ is added to the central angle $\overline{\Delta\theta''}$ to transform the central angle $\overline{\Delta\theta''}$ into an average phase angle $\overline{\Delta\theta'}$ in an original polar coordinate system. By calculating an average phase difference while using a weight coefficient corresponding to the power of each phase signal, the effect of noise on the average phase difference is reduced.

We claim:

1. An ultrasonic Doppler flow meter comprising:
    transmitter-receiver means for transmitting an ultrasonic pulsed continuous wave repeatedly toward an object at predetermined intervals, receiving a reflected wave from the object, and generating a reception signal from the received reflected wave;
    phase detecting means for generating a phase vector indicative of a phase of the reception signal each time the reception signal is generated;
    phase difference detecting means for generating a phase difference value representing a phase difference between a present phase vector and a preceding phase vector each time the phase vector is generated;
    phase difference classifying means for classifying a plurality of phase difference values outputted from the phase difference detecting means into a first group consisting of positive phase difference values and a second group consisting of negative phase difference values;
    means for calculating a first average angle from the phase difference values belonging to the first group and obtaining a cosine value and a sine value of the first average angle;
    means for calculating a second average angle from the phase difference values belonging to the second group and obtaining a cosine value and a sine value of the second average angle;
    means for calculating a weighted sum of the cosine values of the first and second average angles by adding a first product to a second product, the first product being a product of the cosine value of the first average angle and a first weighting coefficient corresponding to the number of phase difference values belonging to the first group, the second product being a product of the cosine value of the second average angle and a second weighting coefficient corresponding to the number of phase difference values belonging to the second group;

means for calculating a weighted sum of the sine values of the first and second average angles by adding a third product to a fourth product, the third product being a product of the sine value of the first average angle and the first weighting coefficient, the fourth product being a product of the sine value of the second average angle and the second weighting coefficient;

means for calculating an argument of a vector from real and imaginary parts of the vector which are equal to the weighted sum of the cosine values and the weighted sum of the sine values, respectively, the argument being a first total average value of the phase difference values outputted from the phase difference detecting means; and means for transforming the first total average value into a flow speed.

2. An ultrasonic Doppler flow meter according to claim 1, further comprising:

means for transforming the phase difference values outputted from the phase difference detecting means into angles in a new polar coordinate system in which a direction of the first total average value serves as a reference axis;

means for adding and averaging the angles in the new polar coordinate system; and means for transforming an output of the adding and averaging means into a value in an original polar coordinate system of the phase difference values outputted from the phase difference detecting means, the value in the original polar coordinate system being a second total average value of the phase difference values outputted from the phase difference detecting means;

wherein the means for transforming transforms at least one of the first total average value and the second total average value into a flow speed.

3. An ultrasonic Doppler flow meter comprising:

transmitter-receiver means for transmitting an ultrasonic pulsed continuous wave repeatedly toward an object at predetermined intervals, receiving a reflected wave from the object, and generating a reception signal from the received reflected wave;

phase detecting means for generating a phase vector indicative of a phase of the reception signal each time the reception signal is generated;

phase difference detecting means for generating a phase difference value representing a phase difference between a present phase vector and a preceding phase vector each time the phase vector is generated;

first averaging means for calculating a first average value of a plurality of phase difference values outputted from the phase difference detecting means by classifying the phase difference values into a first group consisting of positive phase difference values and a second group consisting of negative phase difference values, calculating a first average angle from the phase difference values belong to the first group and decomposing the first average angle into a cosine component and a sine component, calculating a second average angle from the phase difference values belonging to the second group and decomposing the second average angle into a cosine component and a sine component, calculating a weighted sum of the cosine components and a weighted sum of the sine components, and calculating an argument of a vector having a real part equal to the weighted sum of the cosine components and an imaginary part equal to the weighted sum of the since components, the argument being the first average value;

means for obtaining a second average value of the phase difference values outputted from the phase difference detecting means by transforming the phase difference values outputted from the phase difference detecting means into values in a new polar coordinate system in which a direction indicated by the first average value serves as a reference axis, adding and averaging the values in the new polar coordinate system, and transforming the added and averaged values into a value in an original polar coordinate system of the phase difference values outputted from the phase difference detecting means, the value in the original polar coordinate system being the second average value; and means for transforming at least one of the first average value and the second average value into a flow speed.

4. An ultrasonic pulse Doppler flow meter according to claim 3, further comprising a data processor for correcting an error in the second average value by calculating a plurality of presumed average values including fold back errors from the second average value, calculating a plurality of differences between a sum of the phase difference values outputted from the phase difference detecting means and a plurality of sum data based on the plurality of presumed average values each time a phase difference value is outputted from the phase difference detecting means, evaluating the plurality of differences to select one of the plurality of presumed average values most closely representing an actual value of the second average value, and correcting the second average value based on the selected presumed average value.

5. An ultrasonic pulse Doppler flow meter according to claim 3, further comprising means for selecting one of the first average value and the second average value and outputting the selected average value to the means for transforming.

6. An ultrasonic pulse Doppler flow meter according to claim 3, further comprising display means for simultaneously displaying flow speeds transformed from the first average value and the second average value.

7. An ultrasonic pulse Doppler flow meter comprising:

transmitter-receiver means for transmitting an ultrasonic pulsed continuous wave repeatedly toward an object at predetermined intervals, receiving a reflected wave from the object, and generating a reception signal from the received reflected wave;

phase detecting means for generating a power value indicative of a power of the reception signal each time the reception signal is generated;

phase detecting means for generating a phase vector indicative of a phase of the reception signal each time the reception signal is generated;

phase difference detecting means for generating a phase difference value representing a phase difference between a present phase vector and a preceding phase vector each time the phase vector is generated;

phase difference classifying means for classifying a plurality of phase difference values outputted from the phase difference detecting means into a first group consisting of positive phase difference values and a second group consisting of negative phase difference values;

means for calculating a first average angle from the phase difference values belonging to the first group and obtaining a cosine value and a sine value of the first average angle, the first average angle being calculated in accordance with a weighted averaging method in which the phase difference values belonging to the first group are weighted by corresponding power values outputted from the power detecting means;

means for calculating a second average angle from the phase difference values belonging to the second group and obtaining a cosine value and a sine value of the second average angle, the second average angle being calculated in accordance with a weighted averaging method in which the phase difference values belonging to the second group are weighted by corresponding power values outputted from the power detecting means;

means for calculating a weighted sum of the cosine values of the first and second average angles by adding a first product to a second product, the first product being a product of the cosine value of the first average angle and a first sum of power values outputted from the power detecting means corresponding to the phase difference values belonging to the first group, the second product being a product of the cosine value of the second average angle and a second sum of power values outputted from the power detecting means corresponding to the phase difference values belonging to the second group;

means for calculating a weighted sum of the sine values of the first and second average angles by adding a third product to a fourth product, the third product being a product of the sine value of the first average angle and the first sum of power values, the fourth product being a product of the sine value of the second average angle and the second sum of power values;

means for calculating an argument of a vector from real and imaginary parts of the vector which are equal to the weighted sum of the cosine values and the weighted sum of the sine values, respectively, the argument being a first total average value of the phase difference values outputted from the phase difference detecting means; and means for transforming the first total average value into a flow speed.

8. An ultrasonic Doppler flow meter according to claim 7, further comprising:

means for transforming the phase difference values outputted from the phase difference detecting means into angles in a new polar coordinate system in which a direction of the first total average value serves as a reference axis;

means for adding and averaging the angles in the new polar coordinate system; and means for transforming an output of the adding and averaging means into a value in an original polar coordinate system of the phase difference values outputted from the phase difference detecting means, the value in the original polar coordinate system being a second total average value of the phase difference values outputted from the phase difference detecting means;

wherein the means for transforming transforms at least one of the first total average value and the second total average value into a flow speed.

9. An ultrasonic Doppler flow meter comprising:

transmitter-receiver means for transmitting an ultrasonic pulsed continuous wave repeatedly toward an object at predetermined intervals, receiving a reflected wave from the object, and generating a reception signal from the received reflected wave;

phase detecting means for generating a phase vector indicative of a phase of the reception signal each time the reception signal is generated;

phase difference detecting means for generating a phase difference value representing a phase difference between a present phase vector and a preceding phase vector each time the phase vector is generated;

phase difference classifying means for classifying a plurality of phase difference values outputted from the phase difference detecting means into a first group consisting of positive phase difference values and a second group consisting of negative phase difference values;

means for calculating a first total average value of the phase difference values outputted from the phase difference detecting means in accordance with the positive phase difference values of the first group and the negative phase difference values of the second group; and means for transforming the first total average value into a flow speed.

10. An ultrasonic Doppler flow meter according to claim 9, further comprising:

means for transforming the phase difference values outputted from the phase difference detecting means into angles in a new polar coordinate system in which a direction of the first total average value of the phase difference values outputted from the phase difference detecting means serves as a reference axis; and means for calculating a second total average value of the phase difference values outputted from the phase difference detecting means based on the angles in the new polar coordinate system;

wherein the means for transforming transforms at least one of the first total average value and the second total average value into a flow speed.

* * * * *